US008834941B2

(12) United States Patent
Sulaberidze

(10) Patent No.: US 8,834,941 B2
(45) Date of Patent: Sep. 16, 2014

(54) METHOD OF TREATMENT AND PREVENTION OF METABOLIC AND DIGESTION DISORDERS AND OF PATHOLOGICAL STATES ASSOCIATED THEREWITH AND PRODUCTS USED THEREIN

(76) Inventor: Gela Sulaberidze, Tbilisi (GE)

( * ) Notice: Subject to any disclaimer, the term of this patent is extended or adjusted under 35 U.S.C. 154(b) by 636 days.

(21) Appl. No.: 12/627,590

(22) Filed: Nov. 30, 2009

(65) Prior Publication Data

US 2010/0074978 A1 Mar. 25, 2010

Related U.S. Application Data

(63) Continuation of application No. PCT/GE2007/000003, filed on Jul. 2, 2007.

(30) Foreign Application Priority Data

Jun. 1, 2007 (GE) .......................... AP2007010107

(51) Int. Cl.
| | | |
|---|---|---|
| A61K 36/00 | (2006.01) | |
| A23L 1/29 | (2006.01) | |
| A23L 1/10 | (2006.01) | |
| A23L 1/164 | (2006.01) | |
| A23L 1/314 | (2006.01) | |
| A61K 36/889 | (2006.01) | |
| A61K 36/899 | (2006.01) | |
| A23L 1/308 | (2006.01) | |

(52) U.S. Cl.
CPC ............... *A23L 1/296* (2013.01); *A23L 1/1041* (2013.01); *A23L 1/1648* (2013.01); *A23L 1/31436* (2013.01); *A61K 36/889* (2013.01); *A23L 1/1016* (2013.01); *A23V 2002/00* (2013.01); *A61K 36/899* (2013.01); *A23L 1/308* (2013.01)
USPC .......................................... 424/725; 424/777

(58) Field of Classification Search
None
See application file for complete search history.

(56) References Cited

U.S. PATENT DOCUMENTS

| 3,438,780 | A | * | 4/1969 | Singer ........................... 426/623 |
| 4,377,601 | A | * | 3/1983 | Dreese et al. .................. 426/472 |
| 5,223,298 | A | * | 6/1993 | Wullschleger et al. ....... 426/549 |
| 2006/0235282 | A1 | * | 10/2006 | Wesolowski et al. ......... 600/300 |

FOREIGN PATENT DOCUMENTS

| DE | 667245 | C | | 11/1938 |
| DE | 2626734 | A1 | | 12/1977 |
| DE | 3706303 | A1 | | 11/1988 |
| DE | 4007911 | A1 | * | 2/1991 |
| DE | 10337178 | A1 | * | 3/2005 |
| EP | 1629723 | A | | 3/2006 |
| GB | 1510238 | A | | 5/1978 |
| GB | 2026838 | A | | 2/1980 |
| GE | P1998 1205 | B | | 2/1998 |
| GE | P2003 2881 | B | | 2/2003 |
| JP | 58111660 | A | | 7/1983 |
| JP | 59137385 | A | * | 8/1984 |
| JP | 59187745 | A | | 10/1984 |
| JP | 60078566 | A | * | 5/1985 |
| JP | 01098463 | A | * | 4/1989 |
| JP | 2000050819 | A | * | 2/2000 |
| JP | 2007014219 | A | * | 1/2007 |
| KR | 2004036854 | A | * | 5/2004 |
| RU | 2027380 | C1 | | 1/1995 |
| RU | 2136175 | C1 | | 9/1999 |
| WO | WO 9400995 | A1 | * | 1/1994 |
| WO | 01/21012 | A | | 3/2001 |
| WO | 2008/146050 | A1 | | 12/2008 |

OTHER PUBLICATIONS

Wyatt et al, Overweight and obesity: prevalence, consequences, and causes of a growing public health problem, The American journal of the medical sciences, (Apr. 2006) vol. 331, No. 4, pp. 166-174.*
Wilding, Causes of obesity, Practical Diabetes International, (2001) vol. 18, No. 8, pp. 288-291.*
Hansen et al, Causes of obesity and consequences of obesity prevention in non-human primates and other animal models, International textbook of obesity, (2001) pp. 181-201.*
Simpson et al., The prevention of type 2 diabetes-lifestyle change or pharmacotherapy? A challenge for the 21st century. Diabetes Research and Clinical Practice 59 (2003) 165-180.*
Ernsberger et al, Metabolic effects of antihypertensive agents: role of sympathoadrenal and renin-angiotensin systems, Naunyn-Schmiedeberg's Archives of Pharmacology (2006), 373(4), 245-258.*
Metabolic syndrome from Merck manual, accessed on Jun. 2, 2011, pp. 1-2.*
Wisten et al, Fruit and fibre (Pajala porridge) in the prevention of constipation, Scandinavian journal of caring sciences, (Mar. 2005) vol. 19, No. 1, pp. 71-76.*
Granfeldt et al, Metabolic responses to starch in oat and wheat products. On the importance of food structure, incomplete gelatinization or presence of viscous dietary fibre, European journal of clinical nutrition, (Mar. 1995) vol. 49, No. 3, pp. 189-199.*

(Continued)

*Primary Examiner* — Qiuwen Mi
(74) *Attorney, Agent, or Firm* — Gerry J. Elman; Elman Technology Law, P.C.

(57) ABSTRACT

This invention relates to methods for the treatment and prevention of metabolic disorders, digestive disorders, and pathological conditions related thereto whereby a patient is given a nutrient food combination comprising 1) mechanically processed bran and 2) meat or a dried product comprising fruit, vegetables, berries, or any combination thereof. Diluted vinegar may be included.

10 Claims, No Drawings

(56) References Cited

OTHER PUBLICATIONS

Rolled oats from dictionary.com, accessed on Nov. 3, 2011, pp. 1-3.*
Plant from dictionary.com, accessed on Nov. 3, 2011, pp. 1.*
Sulaberidze G, "Margi Bread", http://www.century21.ge/doc/bread.pdf, 2005.
Georgian Research and Development Foundation, "Business Partnership Award Program 2005", http://www.grdf.ge/awards2005.htm.
Beyul, E.A. and Gorunova, N.N., "The Role of Dietary Fiber in Nutrition", Klinicheskaia Meditsina, vol. 65(2), pp. 123-127 (1987). English Abstract.
Marlett, Judith A. et al., "Position of the American Dietetic Association: Health implications of dietary fiber", Journal of the American Dietetic Association, vol. 102 (7), pp. 993-1000 (2002).
Mason, Edward E. and Renquist, Kathleen E., "Gallbladder Management in Obesity Surgery", Obesity Surgery, vol. 12, pp. 222-229 (2002).
Popkin, Barry M., "Part II. What is unique about the experience in lower- and middle-income less-industrialised countries compared with the very-high-income industrialised countries? The shift in stages of the nutrition transition in the developing world differs from past experiences!" Public Health Nutrition vol. 5 (1A), pp. 205-214 (2002).
Shiffman, Mitchell L., et al., "Prophylaxis against Gallstone Formation with Ursodeoxycholic Acid in Patients Participating in a Very-Low-Calorie Diet Program", Annals of Internal Medicine, vol. 122 (12), pp. 899-905 (1995).
Worobetz, L.J., et al., "The effect of ursodeoxycholic acid therapy on gallstone formation in the morbidly obese during rapid weight loss", American Journal of Gastroenterology, vol. 88(10), pp. 1705-1710 (1993). Abstract.
Uusitalo, Ulla, et al., "Dietary Transition in Developing Countries: Challenges for Chronic Disease Prevention", Globalization, Diets and Noncommunicable Diseases, World Health Organization, pp. 6-31[0-25] (2002).

* cited by examiner

METHOD OF TREATMENT AND PREVENTION OF METABOLIC AND DIGESTION DISORDERS AND OF PATHOLOGICAL STATES ASSOCIATED THEREWITH AND PRODUCTS USED THEREIN

CROSS-REFERENCE TO RELATED APPLICATIONS

This is a continuation of international patent application PCT/GE2007/000003 of Gela Sulaberidze, filed Jul. 2, 2007 and published as WO 2008/146050 A1, which claims priority to Georgia AP 2007 010107, filed Jun. 1, 2007, the disclosures of each being incorporated herein by reference.

TECHNICAL FIELD

The invention relates to medicines and concerns the treatment and prevention of metabolic and digestion disorders and of pathological states associated therewith and products used therein.

BACKGROUND ART

The World Health Organization and the absolute majority of professional associations have recognized that improper diet, in particular the high calorie content of the diet, the abundance of carbohydrates and fats, and the deficit of dietary fibers, as the main cause of the development and frequency of most non-transmittable diseases, the so-called civilization-accompanying diseases (myocardial infarction, angina pectoris, atherosclerosis, essential hypertension, cholelithiasis, irritable bowels syndrome, obesity, diabetes mellitus, etc.).

During the world history, the origins of diseases, morbidity, and protection against diseases have always been dependent on the mode of life and diet. The same holds true today. The early populations of humans were hunters and collectors and the reason for the most frequent cause of their morbidity was malnutrition due to starvation episodes. In the beginning of the agricultural period, the transition from collecting and hunting to farming and animal husbandry made the episodes of starvation less frequent. However, the less dynamic mode of life resulted in a growth of infectious and parasitic diseases, frequently associated with chronic malnutrition. Nutrient deficiency increased because of the monotonous diet, especially in wintertime.

Infectious diseases were the main causes of morbidity and mortality during most of the periods of human existence. In the last century, especially during the last decades, the rate of infectious and parasitic, or transmittable diseases, has significantly decreased. The decrease can be ascribed to a rise in the level of education, growth of incomes, industrialization, urbanization, and advances in medical and public health care technologies.

Along with this reduction of infectious and parasitic diseases, there has been a dramatically increase in the rate of non-transmittable diseases or medical conditions, which are now some of the leading causes of mortality. These medical conditions include: myocardial infarction; stenocardia, atherosclerosis, essential hypertension, cholelithiasis, irritable bowels syndrome, obesity, diabetes mellitus, etc. These medical conditions are also known as the civilization-associated diseases because their occurrences are closely associated to changes in the mode of life and living conditions. Incidences of civilization-associated diseases are becoming more frequent. It may be assumed that changes in the mode of life and living conditions may be the main causes of the development of these diseases and may be significant factors of pathogenesis. Changes in the mode of life serve as the basis for the formation and progress of civilization-associated diseases that manifest themselves (or are clinically revealed) in later stages of development when their involution is limited or impossible. At that stage an active drug therapy or surgical treatment is required. Treatments at later stages of the disease generally are more expensive, on the one hand, and are frequently associated with complications that frequently are dangerous to life and dramatically affect the standard of living.

Statistically, the major civilization-associated diseases include metabolic disorders and atherosclerosis, which are usually treated surgically (prosthetics of blood vessels, coronary artery bypass grafting, stenting of blood vessels, etc). These treatments are rather costly and the rate of lethality is high.

From 10 to 15 percent of the world population suffers from cholelithiasis and this number is constantly growing. Each decade of the last 50 years the number of people with cholelithiasis has doubled. To treat the disease, cholecystectomy (excise of gallbladder) is being applied more often. However, such treatment is associated with postoperative complications, digestion and metabolic disorders, development of colon cancer, etc. According to various statistics, in 31 to 72 percent of cases, the post-operated gallbladder nevertheless forms gallstones.

The World Health Organization considers obesity to be an epidemic. Weight loss is one of the decisive factors for treatment and management of the most widespread diseases today. Very often obesity is being treated by means of a reconstructive surgery, which is expensive and is frequently associated with complications.

The weight loss may bring forth negative results without reconstructive surgery as well. Investigations performed at 31 weight management centers in the USA demonstrated that in 28 percent of the 1004 patients, who during 16 weeks, for the purpose of weight loss, were given 520 kilocalories/day in the form of liquid proteins, in the absence of preventive measures, their gallbladders nevertheless form gallstones/concrements.

In order to prevent and/or treat diseases, a patient may have to take chemical drugs, for example statins, chemo drugs, and antidiabetic, antianginal, or hypotensive medications as well as other drugs for a long period or his whole life. Such chemical treatments are had at considerable expenses. These preparations have shown side effects and contraindications, due to which their application is limited. Together with the long clinical course their doses increase revealing changes caused by their side effects that further is a separate problem.

Epidemiologic transformation of diseases, in the first place, is connected with nutrition transformation linked with production of foodstuffs, technologies of production, distribution, availability, changes in dietary habits and physical activities (Glob.).

The industrialization during the last 200 years caused the radical changes in food production, transportation, storage and distribution (Glob.). The economic development together with technological innovations and modern capabilities of marketing caused significant changes to the food content. A quantity of easily assimilated refined carbohydrates and saturated fats has increased in a diet while the quantity of dietary fibers has sharply reduced (Glob.).

Popkin (2002) discusses differences of nutrition transformation between the developed and developing countries. He separated a number of common components characterizing the nutrition transformation in the countries of low and average incomes and concluded that those deviations, in the West of 100-200 years ago, will again occur in the developing world of the last decades.

The incursion of the western habits, for example ways of life and commercial marketing, in developing countries furthers a transfer from the traditional foodstuffs to cheap fats and refined carbohydrates, which are readily available thanks to the globalization. Demographic changes caused by the prolongation of life and reduction of birth rate have a greater impact on the risk factors of the diseases become more urgent, of which improper nutrition is the most important (Glob.).

Analysis of the statistical data accumulated in the $20^{th}$ century has shown the civilization-associated noncontagious diseases to be most frequent in the countries where the population consumes food rich in calories, refined carbohydrates, and fats, and consumes foods poor in dietary fibers.

Dietary fibers contain non-starch polysaccharides and lignin (Beyul E. A. Class. Med. 1987 No 2). In comparison with starch these polysaccharides are not digested by the digestive enzymes and are utilized by the small and large intestines. For that reason from the early $19^{th}$ century and up to the 1960's of the $20^{th}$ century dietary fibers were considered an unnecessary component of food and they even were called the ballast substance. The focus shifted to technologies wherein dietary fibers were separated from the plant stock to produce high-calorie, easily assimilated, refined carbohydrates and fats.

This direction had its opponents. In 1861 the German chemist and nutritionist Justus von Liebig wrote that the separation of bran by sieving of the wheat flour was an excess luxury and that bread baked from groats was more wholesome than white bread. The public and scholars of that time viewed such a statement as absurd. Presently, it has been recognized that Liebig was right.

Both experimental and clinical investigations have proved that dietary fibers regulate digestion and metabolism and act as a physiological stimulator of digestive secretion and gastrointestinal motor activity. As a physiological choleretic, dietary fibers normalize intrarectal pressure, improve hepatoenteral cycle of bile acids, bring forth the sense of satiety, prevent the absorption of exogenous cholesterol, and excrete toxins and other waste products. Therefore, to ensure normal digestion and metabolism, food should contain dietary fibers.

Based on the above, one of the leading ways to prevent and treat the most widespread diseases (myocardial infarction, stenocardia, atherosclerosis, essential hypertension, cholelithiasis, irritable bowels syndrome, obesity, diabetes mellitus, etc.) is to use the practical solution to restrict calorie intake, increase consumption of dietary fibers, and increase dietary fiber content in the diet.

Due to the above, it is logical to assume that at present one of the urgent issues of medicine is the prevention and early treatment of the civilization-associated diseases without chemical preparations and surgical interventions. It is commonly accepted that wholesome food and proper nutrition are among the main means for preventing and early treating. Contemporary principles of proper nutrition undoubtedly employ the limitation of calories at the expense of refined fats and carbohydrates and making up for the deficiency of dietary fibers. It has been ascertained that for the purpose of normal functioning of the organism and prevention of the above diseases, healthy adults should take a minimum of 35-40 g of dietary fiber daily. Children should take more than 5 g daily (Marlett J A 2002). At the same time, low-calorie and dietary fiber-rich food is one of the main components in the treatment of these diseases.

Disorders caused by the deficiency of dietary fibers, and the preventive and therapeutic effect based upon making up of this deficit, has repeatedly proved that the statements by Hippocratus said some twenty-five centuries ago, "do not harm" and "food must be a medication and take drug in the form of food" are still true.

For a modern interpretation of the first statement of Hippocratus ("do not harm") it is necessary to take into account that products rich in dietary fibers are coarse and difficult-to-digest in the unprocessed form. Taking them unprocessed (grain hulls, rinds of fruit and vegetables, berries, etc.) irritates the mucous coat of the stomach, and causes unwanted stimulation of secretion and the motor and evacuation function. Because of the above, the making up of the dietary fibers deficit with unprocessed products containing them in excessive quantities, tablets and granules that contain unprocessed cells is restricted both quantitatively and in time and is, in some cases, even contraindicative. The problem became especially acute in the late $20^{th}$ century and the early $21^{st}$ century, for the consumption of food prepared by the widespread new technologies. Contemporary man, in comparison with his ancestors, is less adapted to consume such coarse food, and the number of patients for whom coarse food is contraindicated is large.

The perfection of the mechanical and thermal processing of food products (sterilization, manufacturing of refined food, concentrated juices) and the invasion of unnatural substances (preservatives) in cookery have significantly reduced the spread of infectious and parasitic diseases and have extended the shelf-life of food. On the other hand, these technological advances changed the content of the foodstuffs, reduced their beneficial properties, and made them unnatural, which in turn has affected the physiological processes, causing digestive and metabolic disorders. The taking of such unnatural food affects the physiological (natural) protective mechanisms of the human organism, making them unable to regulate digestion and metabolism, which is the basis for development of a number of diseases.

There is a ground cereal product (GE Patent 1205, G. Sulaberidze, B. Rachvelishvili, 17 Feb. 1998) comprised of grain flour and mechanically processed bran. Bread prepared from the ground cereal product is used as a wholesome dietary fiber-rich food. There is an improved method for preparing dough from ground cereal product (GE Patent 2881, G. Sulaberidze, 25 Feb. 2003). Bread made of the dough prepared using the method also represents a wholesome dietary fiber-rich food without side effects and contraindications.

From the present state of the art there is no known application of the above ground cereal product and/or finished foodstuff made from it independently or in combination with other foodstuff for the purpose of prevention and treatment of digestion, metabolism and other related diseases. It should, however, be noted that use of the said products for treatment and preventive purposes as the sole foodstuff is inadvisable, for it is connected with the risk of developing a deficiency of proteins, vitamins, microelements.

DETAILED DESCRIPTION OF THE INVENTION

The technical effect of the invention is to enhance the therapeutic and preventive effect provided by processed cereal grain products, and to avoid side effects and contraindications.

The subject matter of the invention comprises a method to provide a nutrient combination containing mechanically processed grain bran and meat or dried product selected from the following group: fruit (preferably berries), vegetables, or any combination thereof.

According to the invention, the bran is selected from the following group: wheat bran, rye bran, corn bran, or any combination thereof.

According to the invention, the meat is selected from the following group: beef, chicken, fish, or any combination thereof.

According to the invention, a nutrient combination may comprise dried fruit including apple, peach, apricot, and other fruits. Dried vegetables, including carrot, beet root, and other vegetables may be components of a nutrient combination. Dried berries, including rosehips, cornel, and other berries may be components of the nutrient combination.

In embodiments of the invention, the nutrient combination (e.g, in the form of a muesli or stuffing) contains components at the following ratio, weight %:

| | |
|---|---|
| Bran | 20-80 |
| Meat or dried product | 20-80 |

According to another embodiment of the invention, the nutrient combination, prepared as a muesli, contains mechanically processed grain bran and dried product selected from the following group: fruit, vegetables, berries, or any combination thereof. Preferably, the dried product is finely minced.

Preferably, the nutrient combination contains components at the following ratio, wt %:

| | |
|---|---|
| Bran | 20-40 |
| Dried product | 60-80 |

The muesli is prepared by known technology: fruit, vegetables, berries or their combination are dried and minced, following which they are mixed with the dispersed bran. Before feeding to a patient or person desiring a dietary fiber-rich food, water or vinegar solution is poured over the muesli and is mixed to produce a porridge ready for consumption.

In a preferred embodiment of the invention a nutrient combination, having the form of a whole product, is fed to a patient or other person. Such food product will additionally contain water or vinegar solution. The preferred concentration of the vinegar solution is 1-5%.

Preferably, the nutrient combination contains components at the following ratio, wt %:

| | |
|---|---|
| Muesli | 20-40 |
| Water or vinegar essence | 60-80 |

In another embodiment of the invention, the nutrient combination is incorporated in a whole food product as a stuffing. The whole product is prepared using known food technology in forming a cutlet or kebab, or is used in stuffed cabbage. One may substitute the cutlets, kebabs, or stuffed cabbage with other foods.

According to the invention, the stuffing contains mechanically processed grain bran, meat and water or vinegar solution. The preferred concentration of the vinegar essence is 1-5%.

According to the invention, the stuffing contains meat selected from the following group: beef, chicken, fish, or any combination thereof. Lean beef is the preferable option.

Preferably, the stuffing contains components at the following ratio, wt %:

| | |
|---|---|
| Bran | 4-48 |
| Meat | 4-48 |
| Water or vinegar solution | the remainder |

The method proposed by the invention is intended for the treatment and prevention of the following disorders and pathological conditions:
Obesity
Diabetes mellitus
Irritable bowel syndrome
Diverticular disease of colon
Constipation
Cholelithiasis
Hypercholesterolemia
Myocardial infarction, stenocardia
Essential hypertension
Constipation due to pregnancy.

The efficacy of the proposed method has been tested on experimental volunteers. As shown in the Examples, the method proposed by the invention is efficient, safe, practicable and cost-effective.

The invention-proposed porridge and stuffing are prepared according to the technology pattern resembling the process of digestion of dietary fibers by the human organism: mechanical processing (oral cavity), processing in the acid medium (stomach), dilution with liquid (oral cavity, stomach). The proposed method enables one to maintain beneficial properties of the dietary fibers and to prevent alteration of the raw material, contraindications and side effects of the food taken. At the same time, the food/nutrient combination used in the method is low-calorie and enables control of the caloric content. Thus, the proposed method makes it possible that both healthy people and patients consume the dietary fiber-rich food without any restriction.

The proposed method can be widely introduced in the objects of public catering providing a good opportunity to widen the practical limits of making up the deficit of dietary fibers and correspondingly to ensure effective prevention of a whole number of pathologies. At the same time, the food combination applied in the method will ensure in the consumer the sense of satiety due to its quantity and its content of dietary fibers. This, in turn, will enable the consumer, where appropriate, to restrict caloric content without affecting physiological processes. Moreover, the proposed method will further the digestion process and the normalization of metabolism.

Thanks to the proposed method, healthy people and patients will consume dietary fibers in the form of natural products proteins, vitamins, minerals, microelements, in which the raw material used to prepare the food combination is rich in dietary fibers (grain hulls, rinds of fruit and vegetables, berries, etc.). Concurrently, it makes possible that the composition of the combination and its beneficial properties be preserved.

The proposed method enables, where necessary, that both healthy and ill people be fed for a long period with the nutrient food combination of the invention without taking other food, so that no deficit of any necessary nutrient (proteins, fats, carbohydrates, vitamins, minerals, microelements, etc.) be developed. The above is very important in terms of both weight control and the prevention and treatment of diseases.

The proposed method, if regularly applied, will enable the contemporary healthy persons make up for the deficit of dietary fibers so that the organism may control the physiological process and prevent thus many disorders and/or pathologies.

EXAMPLES

Example 1

To 50 g muesli containing 20 g wheat bran and 30 g dried apple is added 150 g water and then the combination is mixed to make a porridge to be taken by the patient.

Example 2

To 50 g muesli containing 17.5 g wheat bran, 7.5 g rye bran, 5 g dried apricot, 2.5 g dried beetroot, 2.5 g dried cornel, 2.5 g dried rosehips, and 5 g dried apple is added 75 g of 2% vinegar solution, following which the mass is agitated to make a porridge to be taken by the patient.

Example 3

260 g of 3%-vinegar solution is poured over 175 g wheat bran and agitated before a uniform mass is obtained. Thereafter, the mass is mixed with 65 g minced meat. The stuffing is used to make kebabs to be taken by the patient.

Example 4

115 g wheat bran is poured over with 260 g water and agitated before a uniform mass is produced. The obtained mass is mixed with 75 g minced chicken meat and 50 g fish meat. The stuffing is used to make cutlets to be taken by the patient.

Example 5

Patient: male 54 years old, diagnosis: arterial hypertension (II stage JNC7); hypercholesterolemia (BMI—33.4), left ventricular hypertrophy.
Height—178 cm; weight—109 kg.
Arterial hypertension was systematically observed, which normalization was achieved by hypotensive drugs.
Common cholesterol (CHOL)—285 mg/dl (<80)
High density lipoprotein cholesterol (HDL)—37 mg/dl (>45)
Low density lipoprotein cholesterol (LDL)—175 mg/dl (<A30)
Triglycerides (TG)—364 mg/dl (<200)
For 4 weeks the patient received dietary fiber-rich foods (muesli, mince-based food products).
Loss of weight—6 kg
Blood level of lipids was reduced.
Common cholesterol (CHOL)—217 mg/dl
High density lipoprotein cholesterol (HDL)—58 mg/dl
Low density lipoprotein cholesterol (LDL)—131 mg/dl
Triglycerides (TG)—139 mg/dl

Example 6

Patient: male 42 years old, diagnosis: diabetes mellitus. Type II
Height—182 cm, weight—113 kg.
Glucose in blood: on an empty stomach 104 mg/dl
After taking of a meal—158 mg/dl
Glycated hemoglobin—7.3%

The patient received during one week the dietary fiber-rich, low-calorie food (gruel, mince-based food products).
Glucose in blood: on an empty stomach 101 mg/dl
After taking meals—131 mg/dl
Glycated hemoglobin—6.2%

Example 7

Patient: female, 28-year old; diagnosis—obesity.
For the purpose of weight correction, during 5 weeks took only the gruel and mince-based food products. No contraindications were noted (irritation of mucous coat, undesirable stimulation of secretion and motor-evacuation function); loss in weight 12 kg.

Example 8

Patient: male, 46-year old; diagnosis: irritable bowel syndrome, constipation. Systematically took purgatives. During one week three times a day received 50 g of muesli-based porridge, i.e. gruel. In two days, a daily free defecation was observed.

Example 9

24-year old pregnant; on the 12th week of pregnancy constipation was marked; sense of weight in the right side and hypogastrium. According to the ultrasonic examination, bilious sediment was observable in the gallbladder. Against the background of systematic taking of the gruel and the mince-based food products, constipation was arrested. By ultrasonic examination on the $38^{th}$ week of pregnancy an increase of the bilious sediment and the formation of calculus were not noted.

Example 10

Patient: female, 35 years old.
Height 174 cm, weight 91 kg; body weight index—32 kg/m$^2$.
During 5 weeks for the purpose of weight loss took 520-700 kcal in the form of the dietary fiber-rich food (gruel, mince-based food products).
In two weeks the weight made 86 kg; the body weight index—29 kg/m$^2$.

The above examples are for explanation purposes only and do not restrict the scope of protection of the invention.

REFERENCES APPEARING IN SPECIFICATION

1. Glob
2. Popkin 2002
3. Beyul E. A. Class. Med. 1987 No 2
4. Marlett J A 2002
5. GE Patent 1205, G. Sulaberidze, B. Rachvelishvili, Feb. 17, 1998
6. GE Patent 2881, G. Sulaberidze, Feb. 25, 2003

The invention claimed is:
1. A method for reducing the incidence of and treatment of metabolic disorders selected from the group consisting of obesity and hypercholesterolemia, the method comprising the steps of
 (a) providing a food combination containing (1) 4-48 weight percent mechanically processed grain bran, (2) 4-48 weight percent meat, and (3) the remainder is water or vinegar solution, and

(b) feeding an effective amount of said food combination to a human organism in need thereof for an effective time.

2. The method according to claim 1, characterized in that the grain bran is selected from the group consisting of wheat bran, rye bran, corn bran, and any combination thereof.

3. The method according to claim 1, characterized in that the meat is selected from the group consisting of beef, chicken meat, fish meat, and any combination thereof.

4. The method according to claim 1, characterized in that the food combination has the form of a food product.

5. The method according to claim 1, characterized in that the concentration of said vinegar solution in said food combination is 1-5%.

6. The method according to claim 4, characterized in that the food combination is prepared as a mince or stuffing.

7. The method according to claim 6, characterized in that the meat is selected from the group consisting of beef, chicken meat, fish meat, and any combination thereof.

8. The method according to claim 2, characterized in that the meat is selected from the group consisting of beef, chicken meat, fish meat, and any combination thereof.

9. A method for reducing the incidence of and treatment of metabolic disorders selected from the group consisting of obesity and hypercholesterolemia, the method comprising the steps of
(a) providing a porridge containing (1) 20-40 weight percent muesli, wherein said muesli contains mechanically processed bran and a dried product selected from the group consisting of fruit, vegetables, berries, and any combination thereof, and (2) the remainder water or vinegar solution having a concentration of 1-5%, and
(b) feeding an effective amount of said porridge to a human organism in need thereof for an effective time.

10. The method according to claim 9, characterized in that the muesli comprises 20-80 weight percent mechanically processed bran and 20-80 weight percent dried product.

* * * * *